(12) United States Patent
Nelson et al.

(10) Patent No.: US 10,420,916 B1
(45) Date of Patent: Sep. 24, 2019

(54) DISPOSABLE FLUIDIC SELF-PROPELLING ROBOT FOR TRAVERSING A TUBULAR PASSAGE

(71) Applicant: NUtech Ventures, Lincoln, NE (US)

(72) Inventors: Carl Nelson, Lincoln, NE (US);
Benjamin Terry, Lincoln, NE (US);
Abolfazl Pourghodrat, Broomfield, CO (US); Hossein Dehghani, Lincoln, NE (US); Dmitry Oleynikov, Omaha, NE (US); Prithviraj Dasgupta, Omaha, NE (US)

(73) Assignee: NUTECH VENTURES, Lincoln, NE (US)

( * ) Notice: Subject to any disclaimer, the term of this patent is extended or adjusted under 35 U.S.C. 154(b) by 1127 days.

(21) Appl. No.: 14/618,742

(22) Filed: Feb. 10, 2015

Related U.S. Application Data

(60) Provisional application No. 61/937,695, filed on Feb. 10, 2014.

(51) Int. Cl.
*A61M 25/01* (2006.01)
*A61B 1/31* (2006.01)
*A61M 25/10* (2013.01)

(52) U.S. Cl.
CPC .......... *A61M 25/0155* (2013.01); *A61B 1/31* (2013.01); *A61M 25/10181* (2013.11);
(Continued)

(58) Field of Classification Search
CPC ...... A61F 2/95; A61F 2/2451; A61B 17/3423; A61B 1/00082; A61B 1/31;
(Continued)

(56) References Cited

U.S. PATENT DOCUMENTS 5,595,565 A    1/1997 Treat et al.
6,332,865 B1   12/2001 Borody et al.
(Continued)

FOREIGN PATENT DOCUMENTS

CN    102078177 A    6/2011
KR    20100042185 A    4/2010

OTHER PUBLICATIONS http://www.fujifilmusa.com/products/fujinon_endoscopy/endoscopes/colonoscopes/index.html.
(Continued)

*Primary Examiner* — Tung T Vo
(74) *Attorney, Agent, or Firm* — Jenkins, Wilson, Taylor & Hunt P.A.

(57) ABSTRACT

A probe for traversing a tubular passage includes an introducer to be supported at an entrance to the tubular passage. The probe also includes a probe tip to traverse the tubular passage, and a tube with an inflatable tube segment. In some embodiments, the inflatable tube segment is storable in the probe tip. The inflatable tube segment is configured to be inflated to push the probe tip away from the introducer toward an end of the tubular passage. In some embodiments, the probe includes a sealing mechanism, where the sealing mechanism can be positioned between the inflatable tube segment of the tube and the introducer to maintain the inflatable tube segment in a deflated configuration until inflation of the inflatable tube segment.

15 Claims, 10 Drawing Sheets

(52) U.S. Cl.
CPC ..... *A61M 2205/50* (2013.01); *A61M 2205/52* (2013.01); *A61M 2210/1064* (2013.01)

(58) Field of Classification Search
CPC .......... A61M 25/0155; A61M 2205/52; A61M 2205/50; A61M 25/10181; A61M 25/1064
See application file for complete search history.

(56) References Cited

U.S. PATENT DOCUMENTS

| | | | | |
|---|---|---|---|---|
| 8,002,696 | B2* | 8/2011 | Suzuki | A61B 1/018 600/104 |
| 8,444,549 | B2 | 5/2013 | Viola et al. | |
| 2001/0044595 | A1* | 11/2001 | Reydel | A61F 2/95 604/98.02 |
| 2002/0016607 | A1* | 2/2002 | Bonadio | A61B 17/3423 606/192 |
| 2003/0168068 | A1* | 9/2003 | Poole | A61B 1/00082 128/850 |
| 2007/0015965 | A1* | 1/2007 | Cox | A61B 1/00082 600/114 |
| 2013/0289350 | A1* | 10/2013 | Lerner | A61B 1/005 600/109 |
| 2014/0018625 | A1* | 1/2014 | Lal | A61B 1/31 600/115 |

OTHER PUBLICATIONS

Kim, B., et al., 2006, "Inchworm-like colonoscopic robot with hollow body and steering device," Jsme International Journal Series C-Mechanical Systems Machine Elements and Manufacturing, 49, 205-212.

Yamashita, K., et al., 2013, "Minimally invasive surgery using intraoperative real-time capsule endoscopy for small bowel lesions," Surgical Endoscopy and Other Interventional Techniques, 27, 2337-2341.

Cosentino, Felice, Tumino, Emanuele, Passoni, Giovanni Rubis, Morandi, Elisabetta, Capria, Alfonso, "Functional evaluation of the Endotics System, a new disposable self-propelled robotic colonoscope: in vitro tests and clinical trial", The International Journal of Artificial Organs, 32 (8), 2009, 517-527.

Vucelic, Boris, Rex, Douglas, Pulanic, Roland, Pfefer, Jorge, Hrstic, Irena, Levin, Bernard, Halpern, Zamir, Arber, Nadir, "The Aer-O-Scope: Proof of Concept of a Pneumatic, Skill-Independent, Self-Propelling, Self-Navigating Colonoscope", Gastroenterology, 2006, 130:672, 672-677.

https://my.vanderbilt.edu/stormlab/research/medical-capsule-robots/soft-colonoscopy-platform/.

Zuo, J., G. Yan, and Z. Gao, 2005, "A micro creeping robot for colonoscopy based on the earthworm," J Med Eng Technol, 29, 1-7.

Arezzo, A., et al., 2013, "Experimental assessment of a novel robotically-driven endoscopic capsule compared to traditional colonoscopy," J Digestive and Liver Disease 45, 657-662.

Pourghodrat, A., et al., 2013, "Electro-Hydraulic Robotic Manipulator with Multiple Instruments for Minimally Invasive Surgery" ASME DMD, under review.

Gang, C., et al., 2008, "A semi-autonomous micro-robotic system for Colonoscopy," IEEE International Conference on Robotics and Biomimetics, 703-708.

Valdastri, P., Simi, M., and Webster, R.J., 2012, "Advanced Technologies for Gastrointestinal Endoscopy", Annual Review of Biomedical Engineering, 14(1): p. 397-429.

Kassim, I., Phee, L., Ng, W.S., Gong, F.2006, "Locomotion techniques for robotic colonoscopy", Engineering in Medicine and Biology Magazine, IEEE, 25(3): p. 49-56.

Pourghodrat, A., Dehghani, H., Nelson, C.A., Oleynikov, D., Dasgupta, P., Terry, B.S., 2014, "Disposable Fluidic Self-Propelling Robot for Colonoscopy", Journal of Medical Devices, 8(3): p. 030931-030931.

Glozman, D., Hassidov, N., Senesh, Merav, Shoham, Moshe, Jun. 2010, "A Self-Propelled Inflatable Earthworm-Like Endoscope Actuated by Single Supply Line", IEEE 1(6); 1264-1272.

Eliakim, Rami, Cohen, Lawrence, Segol, Ori, Sightline ColonoSight system for a disposable, power-assisted, non-fiber-optic colonoscopy (with video).—ResearchGate, Gastrointestinal Endoscopy, Jun. 2008, 4.9 DOI: 10.1016/j.gie.2007.12.062, Source: PubMed.

http://www.endotics.com/en.

http://www.pentaxmedical.ca/en/products/endoscopes/lowergastrointestinale/colonoscopes/retroview-colonoscope.aspx.

* cited by examiner

DISPOSABLE FLUIDIC SELF-PROPELLING ROBOT FOR TRAVERSING A TUBULAR PASSAGE

CROSS-REFERENCE TO RELATED APPLICATIONS

The present application claims the benefit under 35 U.S.C. § 119(e) of U.S. Provisional Application Ser. No. 61/937,695, filed Feb. 10, 2014, and titled "Disposable Fluidic Self-Propelling Robot for Colonoscopy," which is herein incorporated by reference in its entirety.

BACKGROUND

The term colonoscopy generally refers to an examination procedure performed on a colon. For example, colonoscopy can be used to evaluate gastrointestinal symptoms of colorectal cancer. Visual diagnosis using a colonoscope-mounted camera can be used to inspect abnormally growing polyps, tumors, inflammation, bleeding, and so forth. In some cases, tissue samples (e.g., polyps) can be collected using a colonoscope and biopsied.

SUMMARY

A probe for traversing a tubular passage includes an introducer to be supported at an entrance to the tubular passage. The probe also includes a probe tip to traverse the tubular passage, and a tube with an inflatable tube segment. In some embodiments, the inflatable tube segment is storable in the probe tip. The inflatable tube segment is configured to be inflated to push the probe tip away from the introducer toward an end of the tubular passage. In some embodiments, the probe includes a sealing mechanism, where the sealing mechanism can be positioned between the inflatable tube segment of the tube and the introducer to maintain the inflatable tube segment in a deflated configuration until inflation of the inflatable tube segment.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

Figure 1:
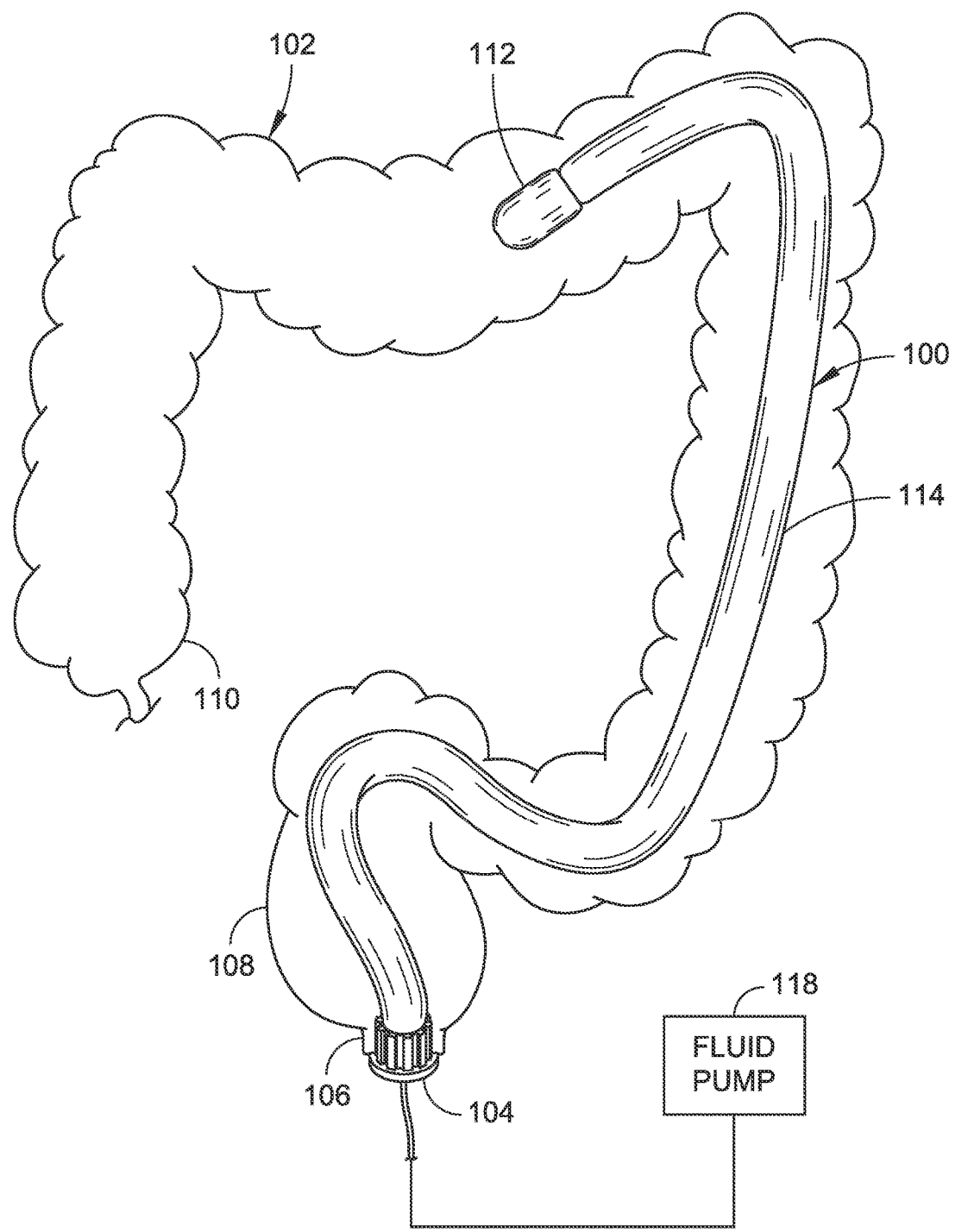
FIG. 1 is a diagrammatic illustration of a probe that can be used to traverse a tubular passage, where the probe is shown in a colonoscopy procedure in accordance with an example embodiment of the present disclosure.
Figure 5:
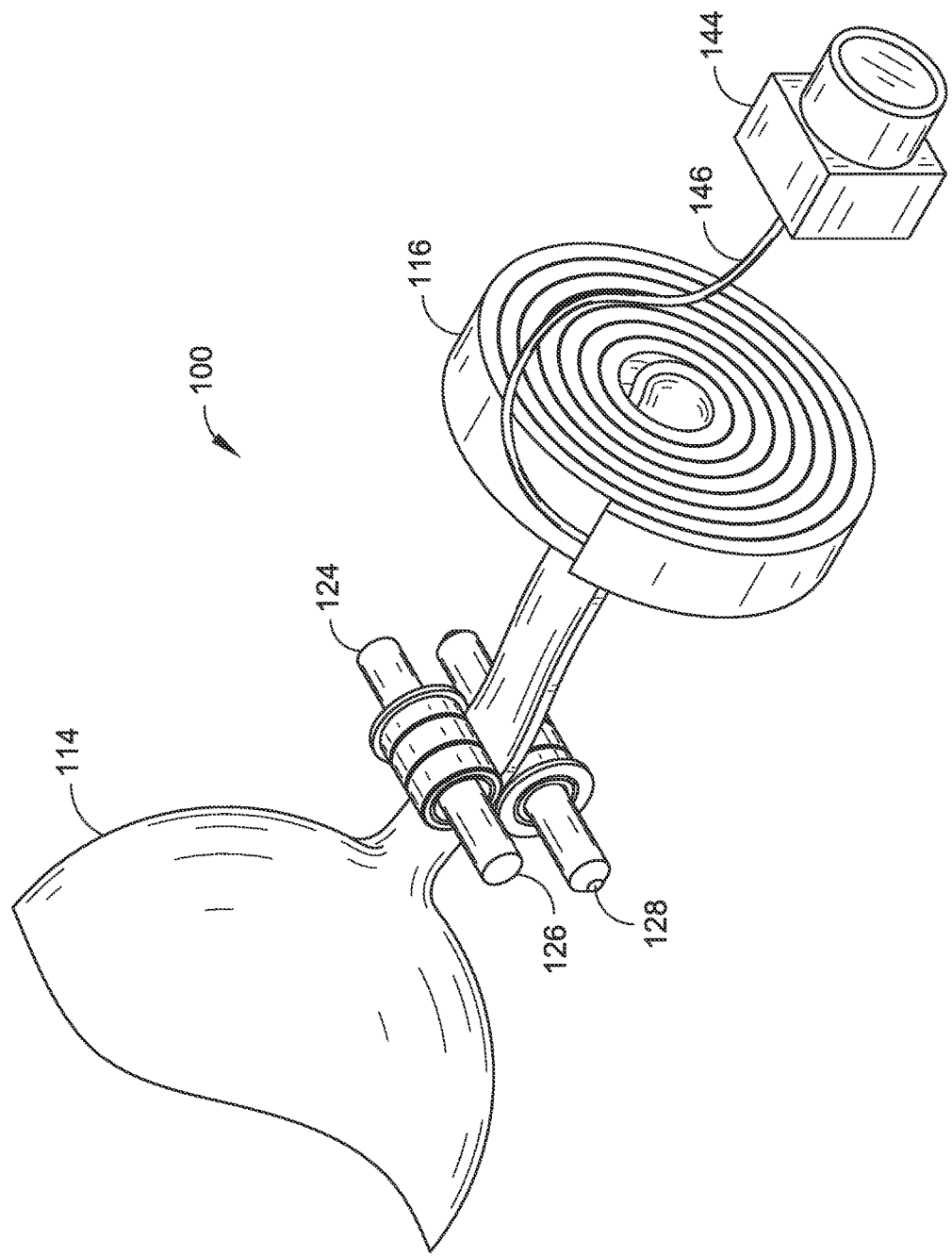

FIG. 5 is a partial isometric view illustrating a probe, such as the probe shown in FIG. 1, where the probe includes a tether that can couple an instrument disposed in a probe tip of the probe to, for example, an external environment, and where the tether is disposed in and/or on a tube comprising an inflatable tube segment stored in the probe tip in accordance with example embodiments of the present disclosure.

Figure 6:
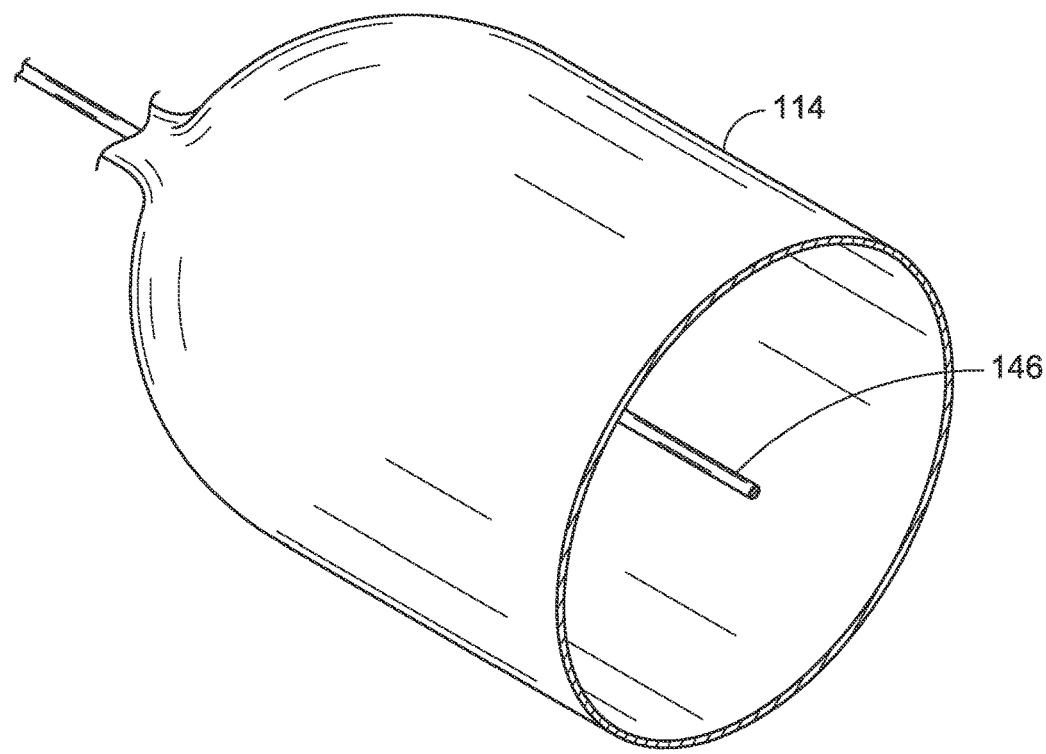

FIG. 6 is a partial cross-sectional isometric view illustrating a tube for a probe, such as the probe shown in FIG. 5, where the tether extends through the tube in accordance with an example embodiment of the present disclosure.

Figure 7:
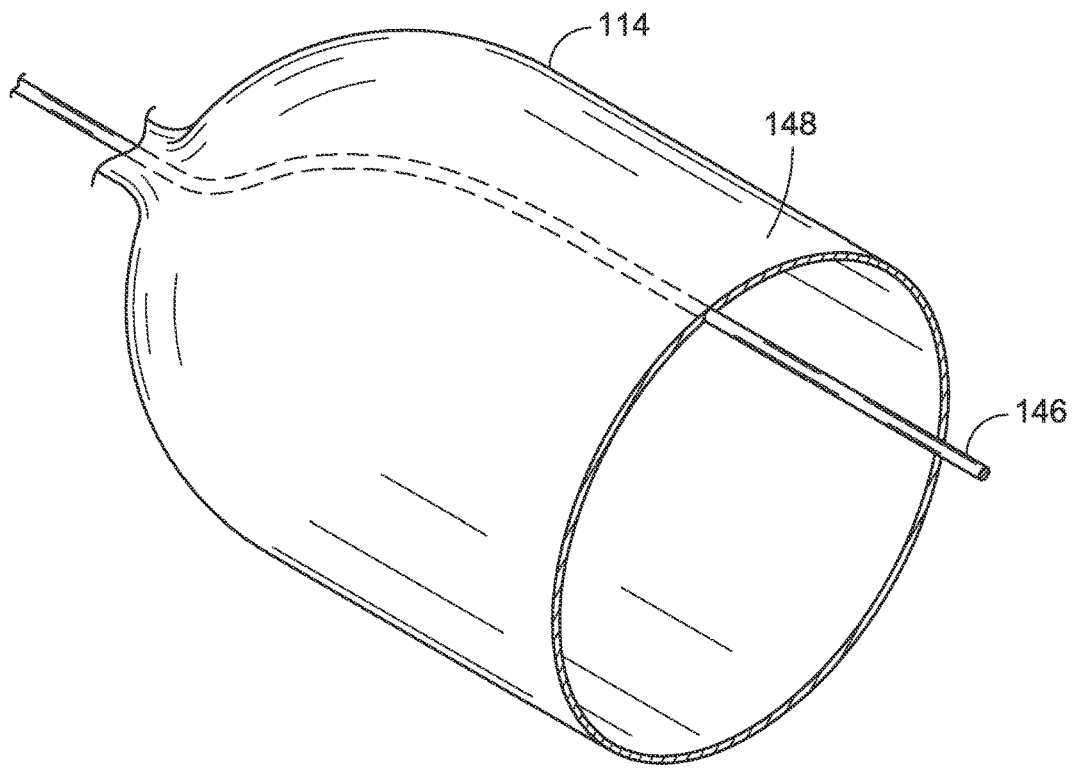

FIG. 7 is a partial cross-sectional isometric view illustrating a tube for a probe, such as the probe shown in FIG. 5, where the tether is disposed in a wall of the tube in accordance with an example embodiment of the present disclosure.

Figure 8:
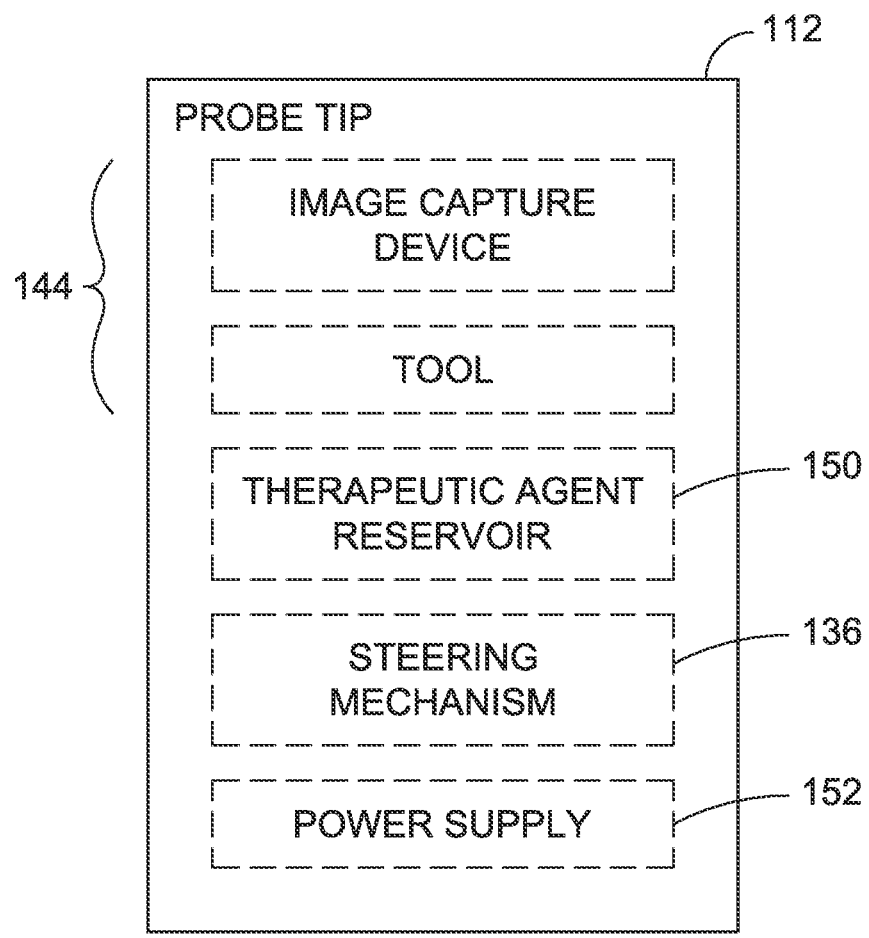

FIG. 8 is a block diagram illustrating a probe tip for a probe, such as the probe shown in FIG. 1, in accordance with example embodiments of the present disclosure.

Figure 9:
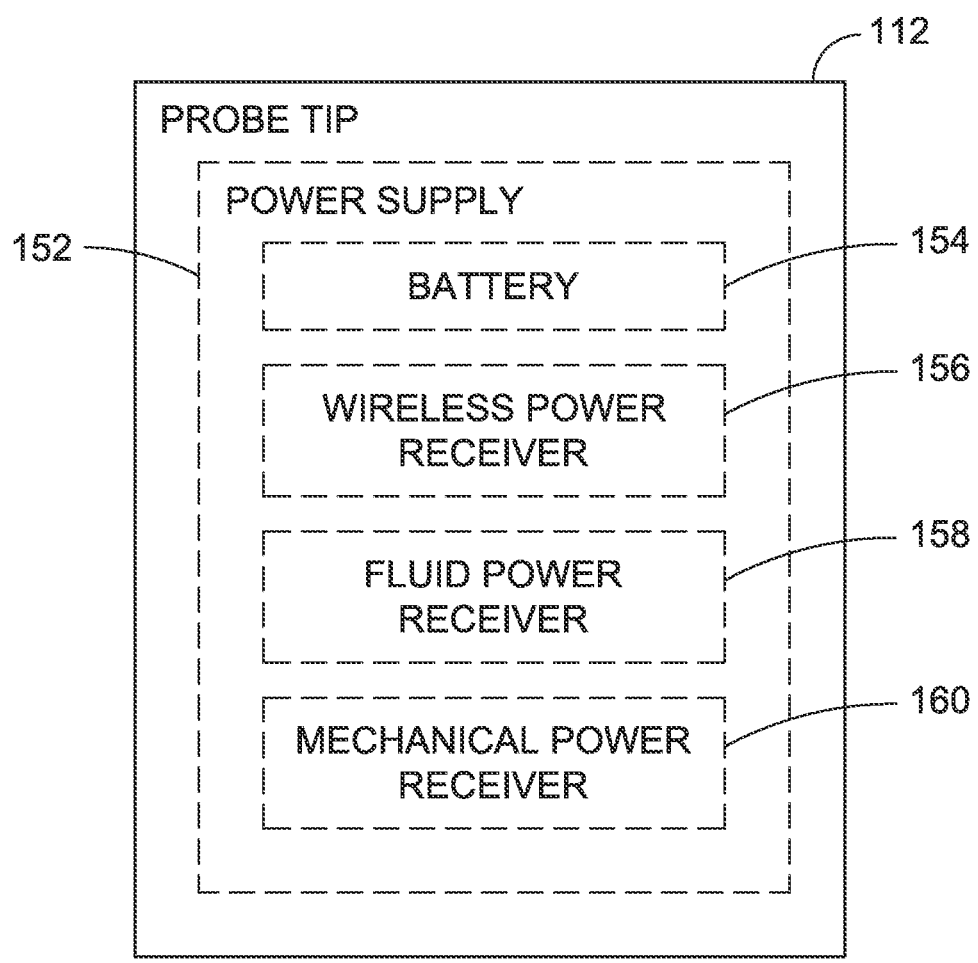

FIG. 9 is another block diagram illustrating a probe tip for a probe, such as the probe shown in FIG. 1, in accordance with example embodiments of the present disclosure.

Figure 10:
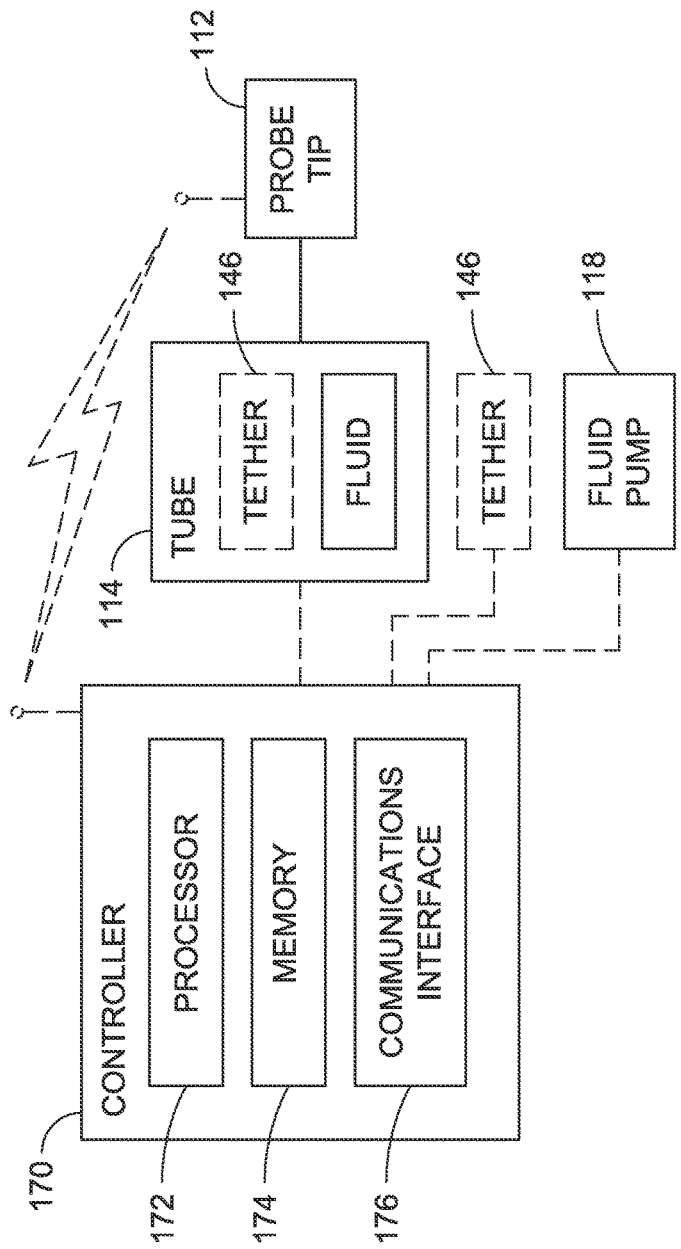

FIG. 10 is a further block diagram illustrating a probe tip for a probe, such as the probe shown in FIG. 1, where the probe tip is communicatively coupled with a controller in accordance with example embodiments of the present disclosure.

Figure 11:
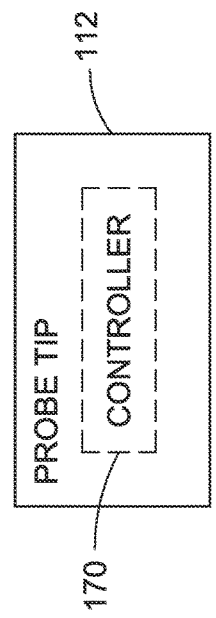

FIG. 11 is another block diagram illustrating a probe tip for a probe, such as the probe shown in FIG. 1, where the probe tip can include a controller in accordance with example embodiments of the present disclosure.

DETAILED DESCRIPTION

Although detection provided by colonoscopy offers many benefits, patients are oftentimes uncomfortable with the procedure, even when under anesthesia. Colonoscopy is generally performed by inserting a long, flexible tube into the colon passing through the anus. This procedure may be accompanied by partial sedation to lessen or preclude a patient's awareness of discomfort. Insufflation of the colon (e.g., pumping of gas into the colon) is also used to open the colon for passage of the colonoscope. However, this technique often presents maneuvering difficulty for the practitioner, as well as the potential for loop formation, and possibly tissue perforation. There can also be a steep learning curve for the practitioner. For example, a highly-trained physician performing a colonoscopy maneuvers a colonoscope by pulling the instrument back and forth, often while applying abdominal support using external hand pressure to straighten the endoscope and allow the scope to move forward. The physician may use markers on the tubing of the colonoscope to gauge the position of the instrument within the colon.

Colonoscopes are generally not disposable, and must be thoroughly cleaned between procedures. In some instances, inchworm-like locomotion, wheels, and/or tracks can also be used to move a colonoscope through a colon. However, these techniques may provide slow advancement of the instrument, as well as relatively large frictional contact with the colon wall. Capsule endoscopy can be used to passively move a capsule instrument through the gastrointestinal tract, which can reduce or eliminate the need for colonoscope insertion and insufflation. However, it can be difficult to control the trajectory of the capsule and/or to localize an identified feature of interest.

Referring generally to FIGS. 1 through 11, a probe 100 for traversing a tubular passage 102, such as a colon, is described. In embodiments of the disclosure, the probe 100 can be used as a colonoscope to perform a colonoscopy. However, a colonoscope is provided by way of example and is not meant to limit the present disclosure. In other embodiments, a probe 100 configured in accordance with the present disclosure can be used for other applications, including other applications involving visual inspection and/or operations performed in other tubular passages, including, but not necessarily limited to: another body lumen, a pipe (e.g., a plumbing pipe), a hole (e.g., a hole drilled through a earthen formation), and so forth. In some embodiments, a probe 100 can move through a colon and into a small intestine connected to the colon.

In embodiments of the disclosure, the probe 100 includes an introducer 104 (e.g., an anal fixture), which can be supported at an entrance 106 to the tubular passage 102 (e.g., at a first end 108 of the tubular passage 102 opposite a second end 110 of the tubular passage 102). The probe 100 also includes a probe tip 112 (e.g., a rigid tip) for traversing the tubular passage 102, and a tube 114 (e.g., a latex tube) including an inflatable tube segment 116 that may be stored in the probe tip 112. The inflatable tube segment 116 can be inflated to push the probe tip 112 away from the introducer 104 toward the second end 110 of the tubular passage 102. For example, a fluid pump 118 can be used to pump fluid (e.g., water, saline solution, etc.) into the tube 114, gradually inflating the inflatable tube segment 116 and pushing the probe tip 112 toward the second end 110 of the colon. The introducer 104 serves as a support while inflating the tube 114 and providing propulsion force to push the probe tip 112 forward (e.g., in the manner of a flexible, linear or curvilinear actuator).

In this manner, the probe 100 can implement robotic locomotion for traversing an irregular tubular passage, such as a colon, a small intestine, and so forth, which can have challenging intrinsic characteristics, such as slippery, naturally collapsed, stretchable wall structures, which may be loosely fixed to surrounding tissue. The probe 100 provides a fluidic self-propelling robot design that can be less invasive, simple, skill-independent, simple to fabricate, inexpensive, disposable, self-steering, and so forth. Further, the probe 100 can be implemented in an autonomous or semi-autonomous robotic platform for diagnostic endoscopy. This configuration can also reduce the invasiveness and discomfort of a procedure such as a colonoscopy.

In embodiments of the disclosure, the tube 114 can be constructed using a soft, flexible, inflatable elastomeric material, which can enhance the noninvasiveness of the procedure. For example, in some embodiments, the tube is constructed from latex (e.g., surgical latex), silicone, and so forth, where the tubing elongates more than it stretches laterally (e.g., inflating in the manner of a balloon). The tubing can facilitate travel of the probe 100 around tight corners within an irregular tubular passage, such as a colon. In some embodiments, a deflated latex tube 114 may comprise an inner diameter (ID) of about one and six-tenths millimeters (1.6 mm) and an outer diameter (OD) of about three and two-tenths millimeters (3.2 mm). However, these dimensions are provided by way of example and are not meant to limit the present disclosure. In other embodiments, tubing with different dimensions can be used. One end of the tube 114 can be affixed to the probe tip 112, and the other end can be connected to a pressurized fluid supply. For example, the tube 114 can be coupled to the fluid pump 118 with a coupling to a rigid and/or semi-rigid tube, such as a polyvinyl chloride (PVC) tube. In other embodiments, the tube 114 can be directly coupled to the fluid pump 118.

In some embodiments, a portion of the inflatable tube segment 116 of the tube 114 can be placed between the introducer 104 and the probe tip 112, while the remainder of the tube 114 can be positioned behind the introducer 104 (e.g., outside of the tubular passage 102). The closed end of the tube 114 proximate to the probe tip 112 can be pre-stressed so that when pressurized fluid is introduced to the tube 114, the tube will begin to inflate from the end of the tube 114 proximate to the probe tip 112 toward the end of the tube 114 proximate to the introducer 104. Then, as the probe tip 112 advances through the tubular passage 102, more of the tube 114 can be pulled in from behind the introducer 104 (e.g., from outside of the tubular passage 102). In this manner, the probe 100 can provide a continuous, long stroke. However, this configuration is provided by way of example and is not meant to limit the present disclosure. In other embodiments, a longer length of the inflatable tube segment 116 of the tube 114 can be positioned between the introducer 104 and the probe tip 112 (e.g., bunched-up, folded, rolled, etc.) and inflated to push the probe tip 112 along the tubular passage 102.

It should be noted that as the probe tip 112 advances, a length of inflated tube 114 behind the probe tip 112 may be pulled along the tubular passage 102 following the probe tip 112, which can generate frictional forces between the tube 114 and an inside surface of the tubular passage 102 (e.g., when the outer diameter of the inflated tube 114 is sufficiently large enough that the tube 114 contacts a wall of the tubular passage 102). In some embodiments, the probe tip 112 and/or the tube 114 can be configured to reduce friction between the tube 114 and a wall of the tubular passage 102. For example, the probe tip 112 and/or the tube 114 can be coated with an ultraviolet (UV) curing adhesive, a hydrophobic spray, and so forth. In some embodiments, several layers of UV-cure adhesive can be applied to the outer surface of the probe tip 112, and the probe tip 112 can also be sprayed with a hydrophobic coating. Further, in some embodiments, the probe tip 112 can be constructed using one or more soft, gel-like materials. Further, a back side of the probe tip 112 proximate to the tube 114 can have a smooth surface and/or surface finish to facilitate retraction of the probe 100 from the tubular passage 102.

In some embodiments, the probe tip 112 can be one and one-quarter inches (1.25 in.) by one and one-quarter inches (1.25 in.) by one and three-quarters inches (1.75 in.). However, these dimensions are provided by way of example and are not meant to limit the present disclosure. In other embodiments, a probe tip with different dimensions can be used. In some embodiments, a rear surface of the probe tip 112 can comprise a shaped surface 120 where the inflated tube 114 contacts the probe tip 112. The surface 120 can be shaped to maintain the end of the inflated tube 114 in contact with the probe tip 112 and effectively transmit propulsive force to the probe tip 112. For example, the surface 120 can comprise a concave shape matching the shape of the inflated tube 114 proximate to the probe tip 112, which may reduce looping and/or buckling of the inflated tube 114.

In some embodiments, the inflatable tube segment 116 of the tube 114 can be stored in the probe tip 112 in a deflated configuration until deployment from the probe tip 112 during inflation of the inflatable tube segment 116. For example, a length of tubing is packed inside the probe tip 112. In this configuration, as the portion of the tube 114 between the introducer 104 and the probe tip 112 is inflated and/or expanded, the inflatable tube segment 116 is pulled out from the probe tip 112, expanding and providing propulsive force for moving the probe tip 112 forward. This configuration can reduce frictional forces between the probe 100 and the inside surface of the tubular passage 102, as there is less relative motion between the inflated tubing and the tubular passage when the tubing is not pulled along the tubular passage 102 following the probe tip 112.

Figure 3:
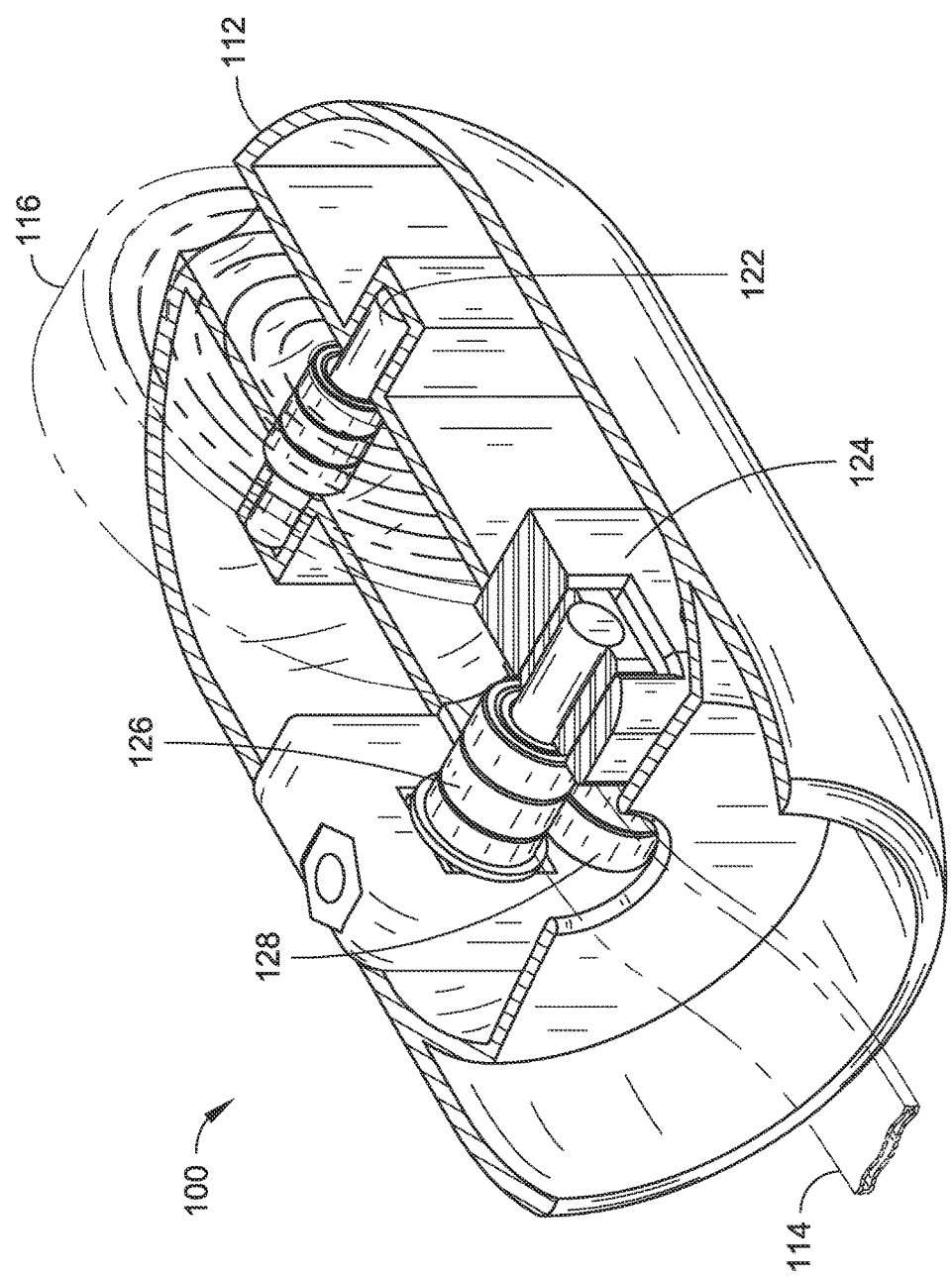
FIG. 3 is a partial cross-sectional isometric view illustrating another probe, such as the probe shown in FIG. 1, in accordance with an example embodiment of the present disclosure.

In some embodiments, the probe tip 112 defines an interior cavity for storing the inflatable tube segment 116. For example, the probe tip 112 includes a first half and a second half in a clamshell configuration, with the inflatable tube segment 116 packed between the two halves. In some embodiments, the inflatable tube segment 116 can be wound (e.g., rolled) around a shaft 122 (e.g., a free-spinning shaft) supported in the probe tip 112 (e.g., as shown in FIG. 3). The shaft 122 can be supported on two bearings, and can include a receiver for accepting a winding instrument for winding the tubing onto the shaft, such as a hex key. Further, the end of the inflatable tube segment 116 can be fixedly attached to the shaft 122 (e.g., glued to the shaft 122, captured by the shaft 122, and so forth). In this configuration, the inflatable tube segment 116 unrolls for deployment from the probe tip 112.

In some embodiments, pressurized fluid can be prevented from entering the inflatable tube segment 116 stored in the probe tip 112. This configuration can prevent or reduce inflation of the inflatable tube segment 116 stored in the probe tip 112, which could otherwise make packing and unpacking the tubing in the probe tip 112 difficult. This configuration can also reduce the amount of volume occupied by the inflatable tube segment 116 stored in the probe tip 112. To reduce or prevent pressurized fluid from entering the inflatable tube segment 116, the probe 100 can include a sealing mechanism 124 disposed in the probe tip 112. The sealing mechanism 124 can be positioned between the inflatable tube segment 116 and the introducer 104 to maintain the inflatable tube segment 116 in a deflated configuration until deployment from the probe tip 112 during inflation of the inflatable tube segment 116.

Figure 2A:
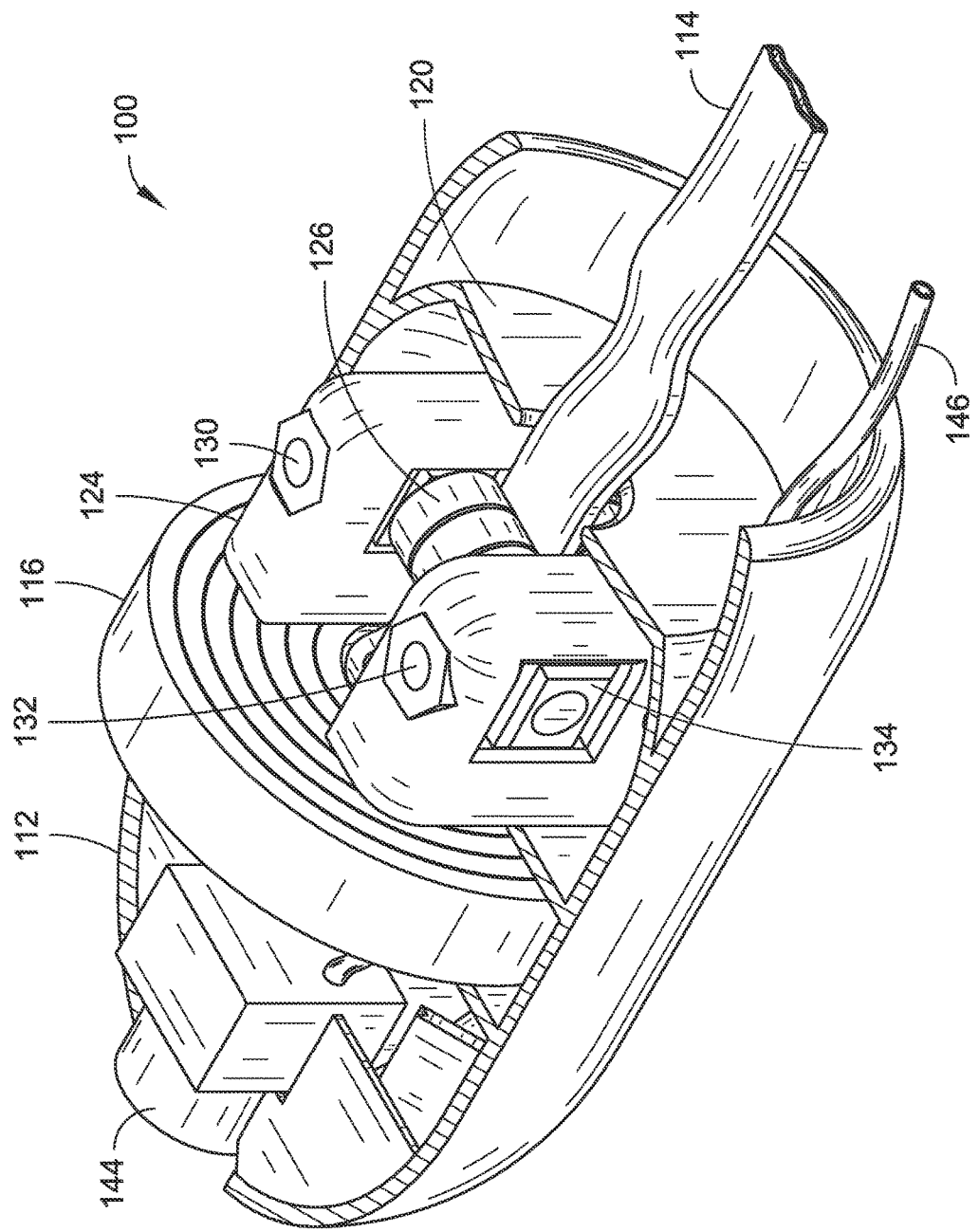
FIG. 2A is a partial cross-sectional isometric view illustrating a probe for traversing a tubular passage, such as the probe shown in FIG. 1, where a tube comprising an inflatable tube segment stored in a probe tip of the probe is shown in a deflated configuration in accordance with an example embodiment of the present disclosure.
Figure 2B:
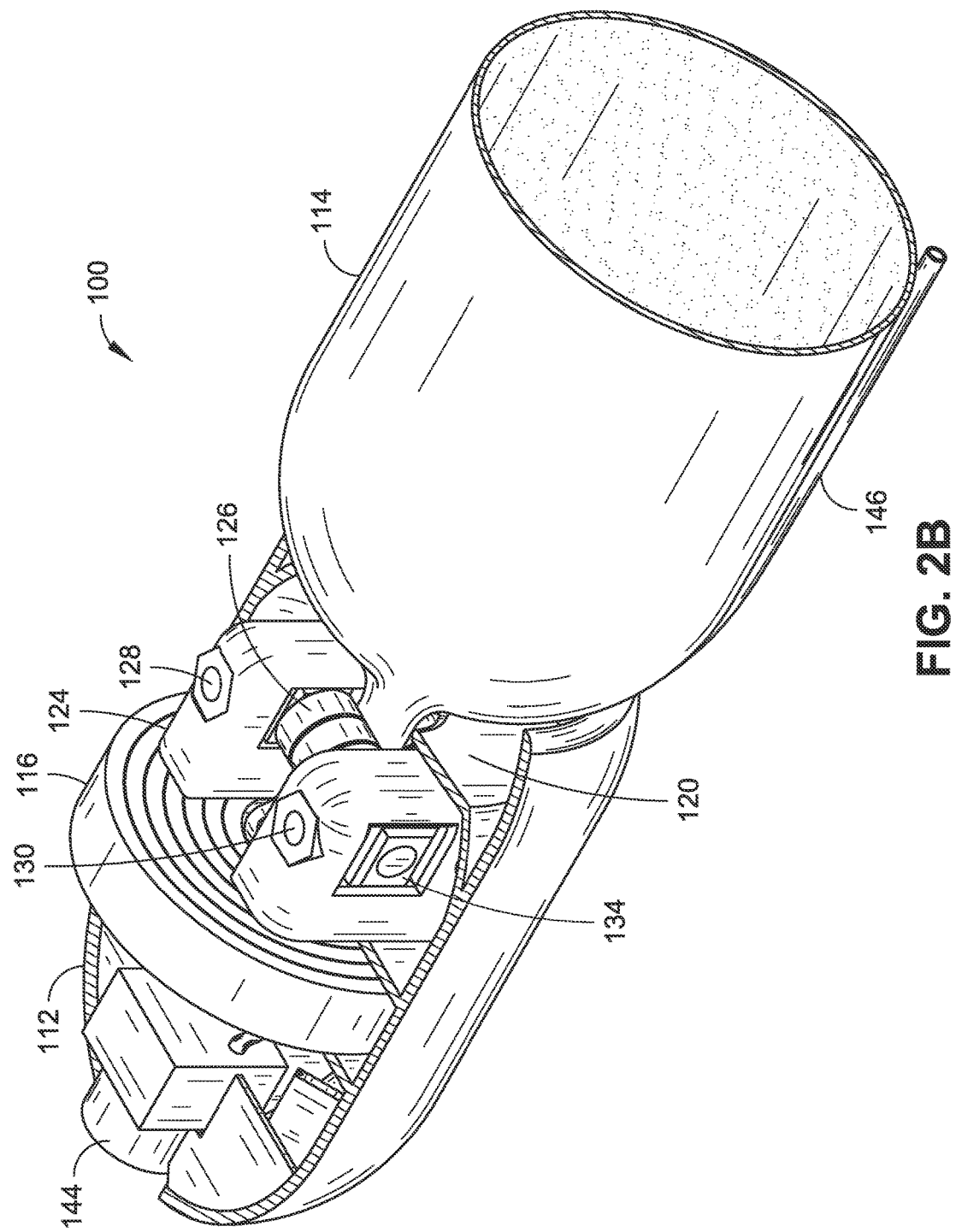
FIG. 2B is a partial cross-sectional isometric view of the probe illustrated in FIG. 2A, where the tube comprising the inflatable tube segment is shown being deployed from the probe tip during inflation of the tube in accordance with an example embodiment of the present disclosure.

In embodiments of the disclosure, the sealing mechanism 124 includes two sets of bearings mounted on two parallel shafts (e.g., a first shaft 126 and a second shaft 128 parallel to the first shaft 126, as shown in FIGS. 2A and 2B). The two bearings press on the tube 114 to prevent fluid from passing through the tube 114 into the probe tip 112. In some embodiments, the distance between the two shafts 126 and 128 can be adjusted to regulate the pressing force on the tube 114 and facilitate sealing and/or smooth movement of the tube through the sealing mechanism 124 (e.g., for winding and/or unwinding of the tube 114). For example two adjustment mechanisms (e.g., a first set screw 130 and a second set screw 132) are used to move the first shaft 126 toward or away from the second shaft 128 to adjust the distance between the shafts 126 and 128. In some embodiments, the first shaft 126 is supported by one or more blocks 134 that are slidably supported by the probe tip 112 and adjustable by the set screws 130 and 132. In operation, one end of the tube 114 can be closed and pressed between the two bearing sets preventing fluid to pass through the sealing mechanism 124 as the tube is pulled into the probe tip 112. As the tubing is pulled in, fluid (e.g., air) is pushed out from the tube 114.

Figure 4:
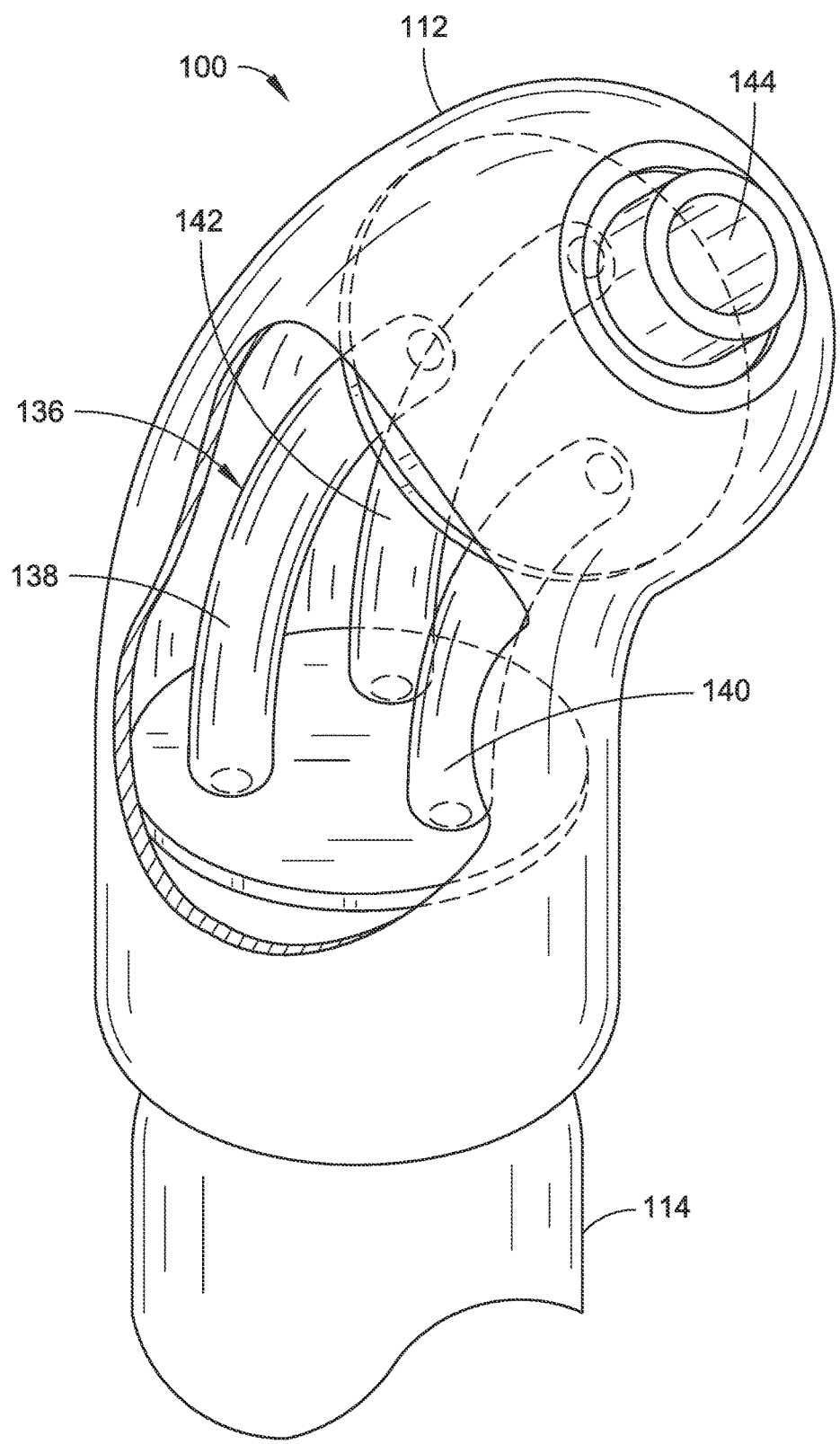
FIG. 4 is a partial cross-sectional isometric view illustrating a probe, such as the probe shown in FIG. 1, where a probe tip of the probe includes a steering mechanism in accordance with example embodiments of the present disclosure.

In some embodiments, the probe 100 can include a steering mechanism 136 (e.g., as shown in FIG. 4). For example, alternating fluid pressure in a first chamber 138, a second chamber 140, and/or a third chamber 142 disposed in the probe tip 112 can be used to tilt the tip of the probe 100, facilitating directional steering through an irregular tubular passage 102, such as a colon. However, this configuration is provided by way of example and is not meant to limit the present disclosure. In other embodiments, the probe tip 112 can include another steering mechanism, such as a ball and socket joint that can be manipulated to steer the tip of the probe 100. In some embodiments, the probe tip 112 can include one or more instruments 144, including, but not necessarily limited to: an image capture device, such as a video camera; a light source, such as one or more light-emitting diodes (LEDs); a biopsy tool, such as forceps; a suction tool; and so forth. The one or more instruments 144 can be deployed from a working channel of the probe tip 112. In some embodiments, directional steering of the probe tip 112, instrument manipulation, and so forth can be implemented as described in U.S. patent application Ser. No. 14/549,182, filed Nov. 20, 2014, and titled "FLUIDICALLY ACTUATABLE DEVICES FOR MINIMALLY INVASIVE SURGERY," which is herein incorporated by reference in its entirety. For example, a fluidically-actuated master-slave control system can be used to achieve fine control for steering.

In some embodiments, a tether 146 is used to connect an instrument 144 disposed in the probe tip 112 to an external environment. For example, the tether 146 can be used to provide power (e.g., electrical power, fluid power (e.g., pneumatic power), and so forth) to one or more instruments 144. In some embodiments, the tether 146 can be routed alongside the tube 114 (e.g., as shown in FIGS. 2A and 2B). However, this configuration is provided by way of example and is not meant to limit the present disclosure. In other embodiments, the tether 146 can be disposed in and/or on the tube 114 (e.g., as shown in FIG. 5). For instance, as shown in FIG. 6, the tether 146 can extend through the tube 114. In another example shown in FIG. 7, the tether 146 can be disposed in a wall 148 of the tube 114. For example, the tether 146 can extend through the wall 148. In another embodiment, the tether 146 can be affixed (e.g., adhered, pressed, etc.) to the wall 148.

Similarly to the inflatable tube segment 116, a portion of the tether 146 can be placed between the introducer 104 and the probe tip 112, while the remainder of the tether 146 can be positioned behind the introducer 104 (e.g., outside of the tubular passage 102). As the probe tip 112 advances through the tubular passage 102, the tether 146 can be fed from behind the introducer 104 (e.g., from outside of the tubular passage 102). In other embodiments, a longer length of the tether 146 can be positioned between the introducer 104 and the probe tip 112 (e.g., bunched-up, folded, rolled, etc.). In still further embodiments, a length of the tether 146 can be packed inside the probe tip 112. In this configuration, as the probe tip 112 advances, the tether 146 can be pulled out (e.g., unrolled) from the probe tip 112. In some embodiments, the tether 146 can also be used to retract the probe 100 from the tubular passage 102.

In some embodiments, the probe 100 can be used to administer a therapeutic agent (e.g., a drug) during a procedure such as a colonoscopy. For example, a therapeutic agent can be stored in a therapeutic agent reservoir 150 in the probe tip 112 (e.g., as shown in FIG. 8). The therapeutic agent can be administered at a selected time and/or location during a procedure. In other embodiments, the therapeutic agent can be gradually released as the probe tip 112 traverses the tubular passage 102. It should also be noted that in some embodiments, an exterior surface of the probe tip 112, the tube 114, one or more selected portions of the tube 114, the tether 146, one or more selected portions of the tether 146, and so forth, can be coated with a therapeutic agent (e.g., an anesthetic), which can be administered during inflation and deployment of the inflatable tube segment 116.

In some embodiments, the probe 100 can include a power supply 152. For example, with reference to FIG. 9, the probe tip 112 can include and/or can be connected to a battery 154, a wireless power receiver 156, a fluid power receiver 158, a mechanical power receiver 160, and so forth. The power supply 152 can be used to power, for example, one or more of the instruments 144 stored in the probe tip 112. In some embodiments, a wireless power receiver 156 can be powered using inductive power transmission. In some embodiments, a fluid power receiver 158 can be used to receive pneumatic power (e.g., from air pressure). In other embodiments, the fluid power receiver 158 can be used to generate electrical current from an alternating magnetic field delivered by ferromagnetic fluid contained in the tube 114 and/or the tubular passage 102. In some embodiments, a mechanical power receiver 160 can be used to generate electrical current from mechanical action of the tubular passage 102 (e.g., muscular contraction proximate to a body lumen).

In some embodiments, power can be delivered to the power supply 152 by the tether 146. For example, a fluid supply tether 146 can be used to supply pneumatic power to a fluid power receiver 158. In other embodiments, an electric cable tether 146 can be used to supply electric current to a battery 154. In further embodiments, a power supply 152 can be located in an external environment (e.g., outside of the tubular passage 102). For example, an external battery and/or AC mains connected to a tether 146 can be used to supply power to one or more of the instruments 144.

Referring now to FIGS. 10 and 11, a probe 100, including some or all of its components, can operate under computer control. For example, a processor can be included with or in a probe 100 to control the components and functions of probes 100 described herein using software, firmware, hardware (e.g., fixed logic circuitry), manual processing, or a combination thereof. The terms "controller," "functionality," "service," and "logic" as used herein generally represent software, firmware, hardware, or a combination of software, firmware, or hardware in conjunction with controlling the probes 100. In the case of a software implementation, the module, functionality, or logic represents program code that performs specified tasks when executed on a processor (e.g., central processing unit (CPU) or CPUs). The program code can be stored in one or more computer-readable memory devices (e.g., internal memory and/or one or more tangible media), and so on. The structures, functions, approaches, and techniques described herein can be implemented on a variety of commercial computing platforms having a variety of processors.

The probe 100 and/or the fluid pump 118 can be coupled with a controller 170 for controlling advancement of the probe tip 112, operation of one or more instruments 144, and so forth. The controller 170 can include a processor 172, a memory 174, and a communications interface 176. The processor 172 provides processing functionality for the controller 170 and can include any number of processors, micro-controllers, or other processing systems, and resident or external memory for storing data and other information accessed or generated by the controller 170. The processor 172 can execute one or more software programs that implement techniques described herein. The processor 172 is not limited by the materials from which it is formed or the processing mechanisms employed therein and, as such, can be implemented via semiconductor(s) and/or transistors (e.g., using electronic integrated circuit (IC) components), and so forth.

The memory 174 is an example of tangible, computer-readable storage medium that provides storage functionality to store various data associated with operation of the controller 170, such as software programs and/or code segments, or other data to instruct the processor 172, and possibly other components of the controller 170, to perform the functionality described herein. Thus, the memory 174 can store data, such as a program of instructions for operating the probe 100 (including its components), and so forth. It should be noted that while a single memory 174 is described, a wide variety of types and combinations of memory (e.g., tangible, non-transitory memory) can be employed. The memory 174 can be integral with the processor 172, can comprise stand-alone memory, or can be a combination of both.

The memory 174 can include, but is not necessarily limited to: removable and non-removable memory components, such as random-access memory (RAM), read-only memory (ROM), flash memory (e.g., a secure digital (SD) memory card, a mini-SD memory card, and/or a micro-SD memory card), magnetic memory, optical memory, universal serial bus (USB) memory devices, hard disk memory, external memory, and so forth. In implementations, the probe 100 and/or the memory 174 can include removable integrated circuit card (ICC) memory, such as memory provided by a subscriber identity module (SIM) card, a universal subscriber identity module (USIM) card, a universal integrated circuit card (UICC), and so on.

The communications interface 176 is operatively configured to communicate with components of the probe 100. For example, the communications interface 176 can be configured to transmit data for storage in the probe 100, retrieve data from storage in the probe 100, and so forth. The communications interface 176 is also communicatively coupled with the processor 172 to facilitate data transfer between components of the probe 100 and the processor 172 (e.g., for communicating inputs to the processor 172 received from a device communicatively coupled with the controller 170). It should be noted that while the communications interface 176 is described as a component of a controller 170, one or more components of the communications interface 176 can be implemented as external components communicatively coupled to the probe 100 via a wired and/or wireless connection. The probe 100 can also comprise and/or connect to one or more input/output (I/O) devices (e.g., via the communications interface 176), including, but not necessarily limited to: a display, a mouse, a touchpad, a keyboard, and so on.

The communications interface 176 and/or the processor 172 can be configured to communicate with a variety of different networks, including, but not necessarily limited to: a wide-area cellular telephone network, such as a 3G cellular network, a 4G cellular network, or a global system for mobile communications (GSM) network; a wireless computer communications network, such as a WiFi network (e.g., a wireless local area network (WLAN) operated using IEEE 802.11 network standards); an internet; the Internet; a wide area network (WAN); a local area network (LAN); a personal area network (PAN) (e.g., a wireless personal area network (WPAN) operated using IEEE 802.15 network standards); a public telephone network; an extranet; an intranet; and so on. However, this list is provided by way of example only and is not meant to limit the present disclosure. Further, the communications interface 176 can be configured to communicate with a single network or multiple networks across different access points.

In implementations, a variety of analytical devices can make use of the structures, techniques, approaches, and so on described herein. Thus, although probes 100 are described herein, a variety of analytical instruments may make use of the described techniques, approaches, structures, and so on. These devices may be configured with limited functionality (e.g., thin devices) or with robust functionality (e.g., thick devices). Thus, a device's functionality may relate to the device's software or hardware resources, e.g., processing power, memory (e.g., data storage capability), analytical ability, and so on.

Generally, any of the functions described herein can be implemented using hardware (e.g., fixed logic circuitry such as integrated circuits), software, firmware, manual processing, or a combination thereof. Thus, the blocks discussed in the above disclosure generally represent hardware (e.g., fixed logic circuitry such as integrated circuits), software, firmware, or a combination thereof. In the instance of a hardware configuration, the various blocks discussed in the above disclosure may be implemented as integrated circuits along with other functionality. Such integrated circuits may include all of the functions of a given block, system, or circuit, or a portion of the functions of the block, system, or circuit. Further, elements of the blocks, systems, or circuits may be implemented across multiple integrated circuits. Such integrated circuits may comprise various integrated circuits, including, but not necessarily limited to: a monolithic integrated circuit, a flip chip integrated circuit, a multichip module integrated circuit, and/or a mixed signal integrated circuit. In the instance of a software implementation, the various blocks discussed in the above disclosure represent executable instructions (e.g., program code) that perform specified tasks when executed on a processor. These executable instructions can be stored in one or more tangible computer readable media. In some such instances, the entire system, block, or circuit may be implemented using its software or firmware equivalent. In other instances, one part of a given system, block, or circuit may be implemented in software or firmware, while other parts are implemented in hardware.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A probe for traversing a tubular passage, the probe comprising:
    an introducer to be supported at an entrance to the tubular passage, the entrance disposed at a first end of the tubular passage;
    a probe tip to traverse the tubular passage;
    a tube comprising an inflatable tube segment storable in the probe tip, the inflatable tube segment to be inflated to push the probe tip away from the introducer toward a second end of the tubular passage opposite the first end; and
    a sealing mechanism disposed in the probe tip, the sealing mechanism positioned between the inflatable tube segment of the tube and the introducer to maintain the inflatable tube segment in the probe tip in a deflated configuration until deployment from the probe tip during inflation of the inflatable tube segment,
    wherein the probe tip defines an interior cavity for storing the inflatable tube segment in the probe tip,
    wherein the sealing mechanism is disposed in the probe tip between the inflatable tube segment of the tube within the probe tip and an inflated segment of the tube extending out of the probe tip, such that, as the probe tip traverses the tubular passage, portions of the inflatable tube segment deploy from the probe tip and are inflated to extend a distance between the probe tip and the introducer at the entrance to the tubular passage;
    wherein the sealing mechanism comprises a first surface and a second surface for pressing the tube there between.

2. The probe as recited in claim 1, wherein the probe tip comprises a concave surface proximate to the tube.

3. The probe as recited in claim 1, further comprising an implement stored in the probe tip.

4. The probe as recited in claim 3, further comprising a tether to connect the implement to a device outside of the tubular passage.

5. The probe as recited in claim 1, further comprising a steering mechanism for steering the probe tip.

6. The probe as recited in claim 1, wherein the sealing mechanism comprises two parallel shafts disposed in the probe tip.

7. The probe as recited in claim 6, wherein the sealing mechanism comprises two sets of bearings mounted on the two parallel shafts.

8. The probe as recited in claim 6, comprising an adjustment mechanism configured for adjusting a distance between the two parallel shafts.

9. The probe as recited in claim 8, wherein the adjustment mechanism comprises first and second set screws.

10. The probe as recited in claim 9, wherein one of the two parallel shafts is supported by one or more blocks that are slidably supported by the probe tip and adjustable by the first and second set screws.

11. The probe as recited in claim 1, wherein the probe tip includes a first half and a second half in a clamshell configuration, and wherein the inflatable tube segment in the probe tip is packed between the first half and the second half.

12. The probe as recited in claim 1, wherein the probe tip comprises a shaft supported in the probe tip, and wherein the inflatable tube segment in the probe tip is wound around the shaft.

13. The probe as recited in claim 12, wherein the shaft is supported on two bearings.

14. The probe as recited in claim 12, wherein the shaft includes a received for accepting a winding instrument for winding the tubing onto the shaft.

15. The probe as recited in claim 12, wherein the inflatable tube segment in the probe tip is fixedly attached to the shaft.

* * * * *